United States Patent [19]

Pankratz

[11] 4,002,736
[45] Jan. 11, 1977

[54] PORCINE BACTERIN

[76] Inventor: Duane C. Pankratz, c/o Grand Laboratories, Freeman, S. Dak. 57029

[22] Filed: Dec. 16, 1974

[21] Appl. No.: 532,771

[52] U.S. Cl. .................................. 424/92; 195/96
[51] Int. Cl.$^2$ .................................. A61K 39/02
[58] Field of Search ............... 424/92; 195/96, 49

[56] References Cited

UNITED STATES PATENTS

| 2,464,197 | 3/1949 | Clarke | 195/123 |
|---|---|---|---|
| 3,625,833 | 12/1971 | Schaffer | 195/96 |
| 3,834,989 | 9/1974 | Harrison | 195/49 |

*Primary Examiner*—Lewis Gotts
*Assistant Examiner*—Cary Owens
*Attorney, Agent, or Firm*—Burd, Braddock & Bartz

[57] ABSTRACT

An adjuvanted *Streptococcus equisimilus* bacterin used to impart specific immunity in swine for *Streptococcus equisimilus* types 1 and 2 and probable cross immunity for types 3 and 4, the method of making the bacterin and the method of immunizing swine with it. The multivalent bacterin is desirably offered with an aluminum hydroxide adjuvant or other adjuvants. It is desirably administered subcutaneously or intramuscularly.

16 Claims, No Drawings

PORCINE BACTERIN

This invention is directed to a porcine *Streptococcus equisimilus* bacterin and more particularly to a porcine mastitis metritis arthritis infertility bacterin produced using *Streptococcus equisimilus* types 1 and 2, Lancefield Group C, and, alternatively or additionally, types 3 and 4. The invention is also directed to the method of making the bacterin and to the method of treating swine therewith.

Since the 1960's *Streptococcus equisimilus* has been isolated from diseased swine at an ever increasing rate of incidence. Veterinary diagnostic laboratories have reported more disease outbreaks due to the etiological agent *Streptococcus equisimilus* than *Erysipelas rhusiopathiae*. Many porcine disease syndromes resembling and frequently diagnosed by practitioners as Erysipelas are (after examination in a qualified laboratory) discovered instead to be caused by *Streptococcus equisimilus*.

Most streptococci isolated from pigs with purulent arthritis have been beta hemolytic *Streptococcus equisimilus*. The sow is the probable source of infection in baby pigs. Characteristically the synovia becomes turbid to purulent and surrounding tissues are inflamed. E. D. Roberts, D.V.M., Ph.D., Ames, Iowa, Am.J.Vet.Res. 29(2):253–262, 1968.

Hemolytic streptococcus in sows is involved in infertility, abortion and stillbirths. J. W. Davis, H. R. Thomas, VM/Sac 61(1):62–63, 1966.

The incidence of streptococcus Lancefield Group C is illustrated by the followng condensed diagnostic report:

Table 26: 1, Page 574: *Diseases of Swine*, 3rd Ed., Dunne

| Lancefield Group | A | B | C | Number of Isolations D | E | F | G | H | K | L | M | N | O | P |
|---|---|---|---|---|---|---|---|---|---|---|---|---|---|---|
| Pigs | 33 | 4 | 236 | 62 | 77 | 2 | 12 | 1 | 8 | 70 | 4 | 11 | 1 | 2 |

*Strepococcus equisimilus* is readily isolated from 30 percent of the tonsils of normal pigs. Shuman, 1969, *Diseases of Swine*, Dunne.

The principal object of this invention, therefore, is to provide a bacterin for immunizing swine against the pathologic effects of *Streptococcus equisimilus*, to provide a method for preparing *Streptococcus equisimilus* bacterin, and a method of administering the same to swine.

The bacterin is prepared from *Streptococcus equisimilus*, Lancefield type C, strains type 1 and type 2 (received from the Veterinary Medical Research Institute, Iowa State University, Ames, Iowa) in the approximate proportions of 50 percent strain $T_1$ and 50 percent strain $T_2$. Bacterin directed specifically to types 3 and 4 may be prepared and administered in the same manner.

The organisms are identified according to those characteristics for *Streptoccus equisimilus* as described in *Bergey's Manual of Determinative Bacteriology*, 7th edition.

*Streptococcus equisimilus* organisms have the following characteristics:

1. Beta hemolysis on defibrinated ovine or bovine blood agar plates both aerobically and anaerobically. Colors are discrete and opaque.

2. Biochemical Reactions: a) Salicin — positive only frequently negative; b) Mannite — negative; c) Inulin — negative; d) Lactose — positive or negative; 3) Raffinose — negative; f) Trehalose — positive; g) Sorbitol — negative; h) Sodium Hippurate — negative; i) Glucose — acid production; also maltose, sucrose, trehalose and glycol; j) Hydrolysis of starch or esculin — negative; k) Gelatin liquification — negative; and l) Lithmus Milk: Acid — positive, Coagulation — negative, Reduction — positive or negative.

3. Glycerol fremented aerobically.
4. Lancefield typing Group C.
5. In fluid media this organism forms a fairly heavy sediment in the bottom of the tube. Some strains show initial clouding of the medium which clears as the culture ages.
6. Microscopic examination of a gram stain reveals it is a gram positive coccus and is 0.5 to 1 micron in length arranged in chains of various length.
7. No capsules are produced.
8. Fibrinolytic.

The virulence of the culture is maintained by passage of the organism through colostrum-deprived piglets, prior to the desiccation of a new seed lot, approximately every 12 to 24 months. Seed lot purity is established at the time of desiccation by cultural characteristics and cellular and colonial morphology. Purity rechecking at the time of seeding is done by microscopic examination and by inoculating both aerobic and anaerobic media to observe growth characteristics and colony morphology.

The production of the bacterin is illustrated by the following:

SEED CULTURES

Seed cultures are carried in Todd Hewitt Broth (Baltimore Biological Laboratories) with a final pH 7.8 ± 0.1. Seed stock maintained at −60° C or lyophilized stock cultures are reconstituted aseptically with 3.0 ml. sterile distilled water with a sterile syringe and needle. A 0.5 ml. volume of this material is inoculated into six seed tubes (25 mm × 200 mm containing 60 ml. of media). The seed cultures are grown for 24 hours at 37.5° C ± 0.5° C. After microscopic examination for purity, 60 ml. of seed culture are inoculated into a 45 l. glass jug of seed media and incubated for 24 hours at 37.5° C ± 0.5° C. The seed cultures of strains $T_1$ and $T_2$ are prepared separately.

PRODUCTION CULTURES

Pyrex glass jugs (or environment controlled bacterial fermenters) are used to grow the production cultures. The production cultures are grown in the following medium with a pH 7.8 ± 0.1:

| | | |
|---|---|---|
| Infusion from | 750,000 | grams Beef Heart |
| Peptonen | 30,000 | grams |
| Dextrose | 3,000 | grams |
| Sodium Chloride | 3,000 | grams |
| Disodium Phosphate | 600 | grams |
| Sodium Carbonate | 3,750 | grams |

| | |
|---|---|
| -continued | |
| Distilled Water Q.S. to | 1,500,000 grams |

Production cultures are inoculated with 2.5% seed by volume from the 45 l. Pyrex jug containing 40 liters of media. Production cultures are grown from 12 to 24 hours at 37.5° C ± 0.5° C.

During the entire growth period all production cultures are observed macroscopically for presence of gross contamination. The production media is observed for characteristic appearance of growth, cell formation, characteristic color, settling of cells and absence of non-typical formation. A microscopic examination is made of the production culture to note the presence of characteristic organisms and the absence of contamination. Any product showing macroscopic or microscopic abnormalities or contamination is killed with 1 percent formaldehyde and discarded. There is not attenuation of the cultures used for the production of this product. Production cultures are evaluated and maintained throughout the production log phase for hydrogen ion and oxygen-carbon dioxide tension. These quality control procedures are also practiced when using continuous flow fermentation systems.

PREPARATION OF THE PRODUCT

The product is harvested at the end of the log growth period. This is about 12 to 24 hours for type 1 and about 18 to 36 hours for type 2. A 100 ml. sample is withdrawn from the production culture. 0.5 ml. formalin is added and the culture is evaluated for cell concentration. After adding at least about 0.5 percent formalin by volume and 5 percent by volume aluminum hydroxide, $Al(OH)_3$, the culture is agitated for about 48 hours and then allowed to settle for about 12 to 72 hours. The amount of aluminum hydroxide added is not critical and greater or lesser amounts between about 1 to 10 percent may be used. After this time the top half of the media is siphoned off using aseptic techniques. The 50 percent supernatant removed is checked for the presence of organisms. The bacterin may also be concentrated by centrifugation.

In addition to the specifications listed above, the media is evaluated for cell concentration utilizing the spectrophotometer. The 100 ml. unconcentrated broth sample must contain at least about $0.5 \times 10^9$ and preferably at least about $1.5 \times 10^9$ organisms for type 1 and type 2. The supernatant of the production media which wa decanted is tested by centrifugation and spectrophotometer to determine if any cells are present. If none are present it is assumed the final production media contains a concentration of at least about $1 \times 10^9$ and preferably at least about $3 \times 10^9$ organisms per ml. This is again verified by the spectrophotometer.

The two antigens are desirably mixed in approximately equal proportion in a 2000 gallon sterilized stainless steel holding tank, although the proportions may vary between about 75:25 to 25:75. The mixture is agitated for about 72 hours. Samples are taken for efficacy tests at this time. The product is filled into 250 cc. plastic or glass serum bottles and then tested for sterility. A 250 ml. bottle is filled with 253 ml. ± ml. using automatic filling equipment. The stopper used is a siliconized flat flange stopper to which is added a one piece aluminum seal. The stoppers are sterilized under pressure.

While one exemplary form of production is described in detail, manufacture of the bacterin can be modified by production in complete environment controlled fermenter. The organism may be lysed by treatment in a cell fractionator which permits the use of a smaller antigenic dose. The use of adjuvant is not critical. Instead of aluminum hydroxide, other adjuvants may be used such as Freund's incomplete adjuvant or other oil base adjuvants or the like. Although the organism strains are desirably separately cultured, grown and harvested, they may be grown together. The cultures may be grown under lighting conditions ranging from full spectrum to total darkness.

The bacterin is administered by injection, either intramuscularly or subcutaneously in doses of from about 2 to 8 ml., and preferably about 5 ml.

Experimental work on swine is summarized as follows:

Experiment 1 was performed to determine which route of inoculation would provide the best challenge route.

Pigs utilized in this experiment were raised on a nearby farm where complete history was known. History and observation revealed no incidence of streptococcus infection. Four week old pigs of either sex were selected at random and placed on an unmedicated feed.

All pigs were challenged with 4 ml. of a 12 hour Todd Hewitt Broth culture containing $2.5 \times 10^9$ organism. (Three pigs were inoculated intramuscularly in the ham with Streptococcus equisimilus strain type 1.) Three pigs were inoculated intraveneously by an intracardial injection with strain type 1. Pigs were necropsied five days post inoculation. The joints routinely examined were the shoulder, elbow, and carpal joints of the frong legs and the coxofemoral, stifle, hock and tarsal joints of the rear legs.

Two of the pigs inoculated by the intracardial route died on day four with lesions typical of streptococcus infection. The organism was re-isolated and identified from both pigs. Eight of fourteen joints revealed lesions of fibrinosuppurative arthritis in the third pig. Streptococcus equisimilus was isolated. No joint lesions were found in any of the pigs vaccinated by the intramuscular route. Bacteriological isolation attempts were negative.

Gross observation of the intramuscular injection site revealed a focal acute hemorrhagic necrotic muscle lesion. No evidence of invasion to other areas of the body was observed grossly.

Experiment 1 showed the intravenous route to be superior to the intramuscular route. An intracardial injection was chosen as the intravenous site because the organism frequently produced lesions of vegetative endocarditis. No such lesions were found however in any of the piglets challenged by the intracardial route. Lesions of fibrinous epicarditis and pericarditis of varying severity were observed in all piglets using the intracardial route.

EXPERIMENT 2 — DETERMINATION OF OPTIMAL CHALLENGE DOSE

Experiment 1 showed that the intravenous route was the more optimal challenge route. Eight week old pigs from the same group utilized in Experiment 1 were used to determine the optimal challenge dose. Both $T_1$ and $T_2$ were tested at three different doses utilizing the intracardial inoculation site. Twelve pigs were utilized for this experiment. Groups of two pigs each were given 0.2 ml., 2 ml., or 20 ml. challenge culture. Challenge cultures were 12 hour Todd Hewitt Broth cultures containing $2.5 \times 10^9$ organisms per ml. After receiving the challenge, the piglets were observed for 5 days. They they were euthanized and necropsied. Lesions were evaluated by bacteriological studies when lesions were questionable.

Experiment 2 revealed that each tenfold dilution produced a lower number of grossly infected joints. The 20 ml. inoculation produced the most satisfactory challenge response. This challenge experiment also revealed that an eight week old pig required a considerably higher challenge dose than full siblings from the same litter did four weeks earlier to produce a similar response. This confirms field observations that the younger pigs are more susceptible.

Experiment 3 was developed to show efficacy of the $T_1$ fraction of the new bivalent *Streptococcus equisimilus* bacterin.

Piglets were utilized from a herd of Yorkshire swine maintained at the research facility. Piglets continued to nurse their dams until four weeks of age at which time they were weaned. No more than three pigs per group were obtained from one litter. Dams were unimmunized and had no history of streptococcus infection. Piglets were ear notched for identification. The first immunizations were performed at 2 weeks of age. The second immunization was given 14 days after the first dose (4 weeks of age). The control pigs received a placebo composed of formalinized Todd Hewitt Broth with 5% aluminum hydroxide as an adjuvant.

Pigs were challenged fourteen days after the last inoculation (6 weeks of age).

The challenge mentioned consisted of 15 ml. of 12 hour Todd Hewitt Broth culture, containing $2.5 \times 10^9$ organism/ml., inoculated by the intracardial method. The more severe challenge dose was chosen because it produced a higher percent of infected joints.

Two groups of immunized pigs were tested. Group A contained ten pigs vaccinated only with the $T_1$ fraction of the bivalent bacterin. Group A received 2.5 ml. of adjuvanted monovalent bacterin containing $2.5 \times 10^9$ organism/ml. into the neck musculature.

Group B contained ten pigs vaccinated intramuscularly with 5 ml. of the $T_1 + T_2$ bivalent bacterin.

Pigs were euthanized and necropsied six days after challenge. The fourteen major joints of the four limbs were evaluated grossly for lesions of fibrinosuppurative arthritis. Any questionable joints were cultured on blood agar plates. Isolation of the organism constituted infection on joints which were questionable upon gross observation.

Two control pigs died on day five. Necropsy revealed a marked septicemia with suppurative arithritis in all joints. Bacteriological studies resulted in re-isolation and identification of *Streptococcus equisimilus* from the joints as well as the liver and kidney. The control pigs had a 70.7% rate of joint infection providing a satisfactory control for evaluating the $T_1$ bacteria. The monovalent $T_1$ bacterin protected 91.7% of joints whereas the combination bacterin protected 85% of the joints. The monovalent bacterin produced better protection than the combination product. When considering only the number of infected joints in the challenge group, the $T_1$ monovalent strain protected 86.9% and the $T_1 + T_2$ bivalent bacterin protected 78.8% of the joints.

Experiment 4 — To determine if efficacy could be produced for the type 2 antigen, another experiment similar to Experiment 3 was performed. Nursing piglets were again obtained from the same Yorkshire swine herd. Three groups of 10 pigs each were obtained at random. No more than three pigs from a litter were used. Group A was immunized intramuscularly in the neck muscle with 2.5 ml. of an aluminum hydroxide adjuvanted bacterin containing $2.5 \times 10^9$ formalin inactivated type 2 organisms. Groups B was immunized at the same site with 5 ml. of aluminum hydroxide adjuvanted bivalent bacterin containing both $T_1$ and $T_2$ strains. This is the same product used in Experiment 3. Control piglets were inoculated intramuscularly with a 5 ml. placebo of formalinized aluminum hydroxide adjuvanted Todd Hewitt Broth. The first dose was administered at two weeks of age. The second dose was administered fourteen days later. The pigs were all challenged fourteen days after the last immunization with 15 ml. of a 12 hour Todd Hewitt Broth culture of $T_2$. Pigs were euthanized and necropsied 6 days later.

The results were similar to those seen with strain $T_1$. The $T_2$ strain monovalent bacterin group had 7.9% of the joints infected. The $T_1 + T_2$ bivalent bacterin group had 11.4% of the joints infected. The control group had only 45% of the joints infected. It appeared as though this group of pigs was much sicker at 4 days of age and necropsy lesions appeared to be regressing. This may indicate that animals should be euthanized earlier. When comparing numbers of infected joints only, the $T_1$ protected 82.5% and the bivalent bacterin protected 74.6% of the joints.

The experimental results are summarized in the tables:

Table I

| | | Determination of Optimal Challenge Dose | | |
|---|---|---|---|---|
| No. Piglets Given Live Strain $T_2$ Challenge | No. Piglets Given Live Strain $T_1$ Challenge | Dosage | $T_1$ % Joints Infected | $T_2$ % Joints Infected |
| 2 | 2 | 0.2 ml. ea. | 6.25 | 12.5 |
| 2 | 2 | 2 ml. ea. | 31.25 | 18.75 |
| 2 | 2 | 20 ml. ea. | 56.25 | 50.00 |

Table II

| | | | | | |
|---|---|---|---|---|---|
| | Comparison of Efficacy of $T_1$ Fraction Utilizing a Monovalent and Bivalent Bacterin | | | | |
| Group | No. Pigs | Dosage | Route of Challenge | No. Joints Infected | % Joints Infected |
| (A) $T_1$ Monovalent | 10 | 2.5 ml. | Intracardial | 12/140 | 9.3 |

Table II-continued

| | Group | Comparison of Efficacy of $T_1$ Fraction Utilizing a Monovalent and Bivalent Bacterin | | | | |
|---|---|---|---|---|---|---|
| | | No. Pigs | Dosage | Route of Challenge | No. Joints Infected | % Joints Infected |
| (B) | $T_1 + T_2$ Bivalent | 10 | 5 ml. | Intracardial | 21/140 | 15 |
| (C) | Controls (Placebo) | 10 | 5 ml. | Intracardial | 99/140 | 70.7 |

Table III

| | Group | Comparison of Efficacy of $T_2$ Fraction Utilizing a Monovalent and Bivalent Bacterin | | | | |
|---|---|---|---|---|---|---|
| | | No. Pigs | Dosage | Route of Challenge | No. Joints Infected | % Joints Infected |
| (A) | $T_2$ Monovalent | 10 | 2.5 ml. | Intracardial | 11/140 | 7.9 |
| (B) | $T_2 + T_1$ Bivalent | 10 | 5 ml. | Intracardial | 16/140 | 11.4 |
| (C) | Placebo (control) | 10 | 5 ml. | Intracardial | 63/140 | 45 |

The embodiments of the invention in which an exclusive property or privilege is claimed are defined as follows:

1. A bacterin for prophylactic treatment of the pathologic effects of the bacterium Streptococcus equisimilus in swine, which bacterin consists essentially of killed Streptococcus equisimilus bacteria suspended in an injectable aqueous medium.

2. A bacterin according to claim 1 further characterized in that said bacterin includes killed Streptococcus equisimilus, Lancefield Group C, strains $T_1$ and $T_2$ in proportion between about 75:25 to 25:75.

3. A bacterin according to claim 1 further characterized in that said killed Streptococcus equisimilus is present in amount at least about $1 \times 10^9$ organisms per ml.

4. A bacterin according to claim 1 further characterized in that said bacterin is adjuvanted with aluminum hydroxide.

5. A method of making a bacterin for prophylactic treatment of the pathologic effects of Streptococcus equisimilus in swine, which method comprises:
 A. inoculating a liquid nutrient medium with a culture of live Streptococcus equisimilus,
 B. incubating said culture for about 12 to 36 hours under growth-promoting temperature conditions,
 C. adding a bacteria killing agent to said incubated culture,
 D. concentrating the culture by separation,
 E. packaging the resultant bacterin for administration.

6. A method according to claim 5 further characterized in that:
 A. Streptococcus equisimilus, Lancefield Group C, strains $T_1$ and $T_2$ are separately cultured, grown and harvested, and
 B. the separate products are admixed prior to packaging.

7. A method according to claim 6 further characterized in that:
 A. said strain $T_1$ culture is incubated for about 12 to 24 hours at about 37° C, and
 B. said strain $T_2$ culture is incubated for about 18 to 36 hours at about 37° C.

8. A method according to claim 5 further characterized in that aluminum hydroxide is added with the bacteria killing agent as an adjuvant.

9. A method according to claim 7 further characterized in that said adjuvant is added in the amount of about 1 to 10 percent.

10. A method according to claim 5 further characterized in that said killing agent is 40 percent formalin added to the extent of at least about 0.5 percent of the incubated culture.

11. A method for prophylactic treatment of pathologic effects of the bacterium Streptococcus equisimilus in swine, which method comprises injecting swine with a bacterin including the killed bacteria Streptococcus equisimilus.

12. A method according to claim 11 further characterized in that said bacterin is an aluminum hydroxide adjuvant.

13. A method according to claim 11 further characterized in that said bacterin is administered as a stable aqueous suspension of killed Streptococcus equisimilus.

14. A method according to claim 13 further characterized in that said bacterin is administered by intramuscular or subcutaneous injection in dosages of about 2 to 8 ml. per animal.

15. A method according to claim 13 further characterized in that said killed Streptococcus equisimilus is present in amount at least about $1 \times 10^9$ organisms per ml.

16. A method according to claim 11 further characterized in that said bacterin includes killed Streptococcus equisimilus, Lancefield group C, strains $T_1$ and $T_2$ in proportion between about 75:25 to 25:75.

* * * * *

UNITED STATES PATENT AND TRADEMARK OFFICE
CERTIFICATE OF CORRECTION

PATENT NO. : 4,002,736
DATED : January 11, 1977
INVENTOR(S) : Duane C. Pankratz

It is certified that error appears in the above-identified patent and that said Letters Patent are hereby corrected as shown below:

Column 3, line 20, "not" should be --no--

Column 3, line 51, "wa" should be --was--.

Column 3, line 64, before "ml." (third occurrence), --1-- is omitted.

Column 4, line 35, "frong" should be --front--.

Signed and Sealed this

Fifteenth Day of March 1977

[SEAL]

Attest:

RUTH C. MASON
*Attesting Officer*

C. MARSHALL DANN
*Commissioner of Patents and Trademarks*